(12) United States Patent
Bettenhausen et al.

(10) Patent No.: US 8,272,508 B2
(45) Date of Patent: Sep. 25, 2012

(54) MODULAR CONTAINER FOR MEDICAL INSTRUMENTS AND IMPLANTS WITH FLEXIBLE EDGE HOLDERS

(75) Inventors: Todd E. Bettenhausen, Indianapolis, IN (US); Cary A. Bettenhausen, Indianapolis, IN (US)

(73) Assignee: ContainMed, Inc., Speedway, IN (US)

( * ) Notice: Subject to any disclaimer, the term of this patent is extended or adjusted under 35 U.S.C. 154(b) by 223 days.

(21) Appl. No.: 12/900,585

(22) Filed: Oct. 8, 2010

(65) Prior Publication Data
US 2012/0085720 A1  Apr. 12, 2012

(51) Int. Cl.
*B65D 83/10* (2006.01)
*A61L 2/00* (2006.01)

(52) U.S. Cl. ........................................ 206/370; 422/300

(58) Field of Classification Search .................. 211/60.1, 211/69, 69.1, 69.2, 69.3, 69.4, 70.6, 70.7, 211/85.13, 85.18, 86.01, 183, 184; 248/213.2, 248/220.31, 220.41, 220.42, 220.43; 206/363, 206/370, 372, 373, 438, 439, 565; 422/297, 422/300
See application file for complete search history.

(56) References Cited

U.S. PATENT DOCUMENTS

| | | | | |
|---|---|---|---|---|
| 1,939,497 A * | 12/1933 | Herring | ........................ | 206/207 |
| 4,135,868 A * | 1/1979 | Schainholz | ................... | 422/310 |
| 4,798,292 A | 1/1989 | Hauze | | |
| 5,384,103 A | 1/1995 | Miller | | |
| 5,492,671 A * | 2/1996 | Krafft | .............................. | 422/26 |
| 5,681,539 A | 10/1997 | Riley | | |
| 5,725,097 A | 3/1998 | Bettenhausen et al. | | |
| 5,759,502 A * | 6/1998 | Spencer et al. | ............... | 422/300 |
| 5,896,987 A | 4/1999 | Bettenhausen | | |
| 6,099,812 A | 8/2000 | Allen et al. | | |
| 6,164,738 A | 12/2000 | Dane et al. | | |
| 6,193,932 B1 * | 2/2001 | Wu et al. | .......................... | 422/28 |
| 6,244,447 B1 * | 6/2001 | Frieze et al. | ............... | 211/85.13 |
| 6,331,280 B1 * | 12/2001 | Wood | ............................ | 422/300 |
| 6,382,575 B1 * | 5/2002 | Frush et al. | .............. | 248/220.31 |
| 7,341,148 B2 * | 3/2008 | Bettenhausen et al. | ........ | 206/370 |
| 7,717,264 B2 | 5/2010 | Bettenhausen et al. | | |
| 7,722,837 B2 * | 5/2010 | Riley | ............................ | 422/300 |
| 7,748,529 B2 * | 7/2010 | Foreman et al. | ............. | 206/370 |
| 7,861,860 B2 * | 1/2011 | Bettenhausen et al. | ........ | 206/370 |
| 8,069,998 B2 * | 12/2011 | Thomas | ...................... | 211/85.13 |
| 2002/0074253 A1 * | 6/2002 | Allen et al. | .................... | 206/370 |
| 2006/0213794 A1 * | 9/2006 | Foreman et al. | ............. | 206/370 |
| 2007/0205123 A1 * | 9/2007 | Bettenhausen et al. | ........ | 206/363 |
| 2009/0146032 A1 * | 6/2009 | Bettenhausen et al. | .. | 248/220.31 |
| 2009/0266728 A1 * | 10/2009 | Turner et al. | ................... | 206/363 |

* cited by examiner

*Primary Examiner* — Darnell Jayne
*Assistant Examiner* — Joshua Rodden
(74) *Attorney, Agent, or Firm* — Woodard Emhardt Moriarty McNett & Henry LLP (57) ABSTRACT

A sterilization container having surgical implement/implant holders with flexible edges. Each holder is in the form of a pair of brackets which are positioned tightly on either side of a flexible wall for cooperatively forming a composite holder with an upwardly opening recess. The flexible wall of each holder extends beyond edges of its respective pair of brackets for forming the flexible edges which are used to support the surgical implements/implants. Outwardly turned feet on the bottom of each of the pair of brackets are placed through holes on a base wall of the sterilization container for securing each holder to the container.

11 Claims, 6 Drawing Sheets

MODULAR CONTAINER FOR MEDICAL INSTRUMENTS AND IMPLANTS WITH FLEXIBLE EDGE HOLDERS

BACKGROUND OF THE INVENTION

1. Field of the Invention

The present invention relates generally to the field of sterilization containers having holders for removably securing surgical instruments and implants within the containers.

2. Description of the Prior Art

Various types of containers and cases have been provided to organize surgical instruments, implants and other medical devices. These items must not only be organized but protected from damage. Likewise, the items must be sterilized, stored and then delivered for ready use. In our U.S. Pat. No. 5,725,097, we have disclosed an instrument cassette and sterile wrap assembly composed of a tray and a lid mounted thereto. In our U.S. Pat. No. 5,759,502 we have disclosed an instrument cassette having a mechanism to prevent lateral movement of the medical instrument when positioned within the cassette. In our U.S. Pat. No. 5,896,987 the tray is provided with downwardly extending feet that are nestable within recesses provided in the tray cover located there beneath. In our U.S. Pat. No. 6,164,738 the storage and sterilization tray assembly is designed to be slidably mounted on a horizontally extending rack.

The sterilization and storage tray assemblies must be modified or tailored to the particular size and configuration of the instruments, implants and devices to be held within the tray. Various types of brackets and holders are typically mounted within the tray assembly with the configuration of the brackets depending upon the items to be held within the assembly. In order to utilize the tray assembly in a variety of different applications, it is desirable to provide a tray assembly having internal brackets that may be easily moved or changed depending upon the items to be held by the brackets. Disclosed herein is such a tray assembly.

One such bracket we have devised is disclosed in our U.S. Pat. No. 7,717,264. The bracket shown in FIGS. 29-34 is particularly useful in partitioning the container into multiple compartments through the use of a bar mounted to a plurality of rigid brackets holding the bar to a base plate or the floor of a container. The bar is produced from a flexible material, such as, silicone rubber thereby allowing the bar to be cut and shaped to hold a variety of differently configured medical items. The length of a bracket produced from a flexible material is limited when vertical posts are used to mount the bracket since the material will flex an undesirable amount. The flexible bar shown in FIG. 29 on the other hand is secured along its length thereby limiting the amount of flexibility.

Despite the prior containers and brackets, there is a need for providing brackets or holders within the sterilization containers that may be easily installed and removed without requiring disassembly of various fasteners. In U.S. Pat. No. 5,681,539 there is disclosed a surgical instrument retention bracket having brackets extending through the floor with a c-ring then releasably engageable with the tip of the bracket pillar. Another approach is shown in U.S. Pat. No. 4,798,292 wherein the bracket pillars include spring bottom portions that are extendable through a wall and releasably secured thereto. In U.S. Pat. No. 6,099,812, a sterilization tray with removable instrumentation wall is disclosed that has a lengthwise extending bottom edge portion extendable through a wall for mounting purposes. The bottom edge portion extends outward of either side of the holder. A similar approach is disclosed in U.S. Pat. No. 5,384,103.

In order to prevent marring or damage to the various surgical instruments and implants positioned in the container holders, it is desirable to provide a cushion edge holder with the holder still exhibiting structural rigidity along its length and height. Disclosed herein is a composite holder having a pair of rigid side walls between which is located a flexible wall extending beyond the edges of the two side walls thereby providing a holder having a cushioned edge. Further, the components of the composite holder are secured together by fasteners extending through the top portions of the components whereas outwardly turned feet are positioned on either side of the holder along its bottom edge portion forcing the components together when the holder is mounted to a wall.

SUMMARY OF THE INVENTION

One embodiment of the present invention is a sterilization container for holding medical items therein and comprising a five sided tray having a base with holes extending through the base. The tray has upwardly extending side walls. A plurality of bracket combinations are removably mounted to the base for releasably holding the medical items within the tray. The bracket combinations include a pair of mutually opposed and spaced apart vertically extending walls each with outwardly turned feet with said bracket combinations extending through the holes of the base holding the walls perpendicular relative to the base with the feet integrally attached to the walls. An elongated silicone bar is located between the walls with a plurality of fasteners extending through the bar and the walls tightly securing the walls to the bar. The bar has length and height with the walls extending along and beyond the length and along and beyond the height providing a cushion edge portion outwardly of the walls.

Another embodiment of the present invention is a bracket arrangement holding medical items on a base wall for sterilization. A first bracket has a rigid first main body with a plurality of first feet integrally attached thereto and extending there beneath in a first outward direction from the first main body at an approximate included angle of ninety degrees so that when the bracket is extended through a base wall and arranged thereto, the first main body is above the base wall and arranged perpendicular to the base wall. A second bracket has a rigid second main body spaced apart from the first main body and having a plurality of second feet integrally attached thereto and extending there beneath in a second outward direction opposite to the first direction and away from the first plurality of feet at a second included angle relative to the second main body of approximately ninety degrees so that when the second bracket is extended through the base wall and arranged thereto, the second main body is above the base wall and arranged perpendicular to the base wall. An elongated bar of flexible material extends along the length of the first bracket and the second bracket and is positioned there between. A plurality of fasteners extend through the first bracket, the elongated bar and the second bracket securing the combination together. The first main body, the second main body, the plurality of the first feet and the plurality of the second feet are of equal thickness with the first feet and the second feet extendable through a base wall for securing the bracket arrangement thereto. The first included angle and the second included angle are equal, and position the first main body and the second main body in a parallel relationship. The elongated bar extends outwardly of the rigid first main body and the rigid second body providing a flexible contact edge for medical items to be held by the bracket arrangement.

It is an object of the present invention to provide a new and improved sterilization container for medical instruments and implants.

Yet a further object of the present invention is to provide holders within sterilization containers that have cushioned edge portions to contact the items held.

A further object of the present invention is to provide a composite bracket arrangement that exhibits structural rigidity along its length and height while providing a flexible cushioned edge.

Related object and advantages of the present invention will be apparent from the following description.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
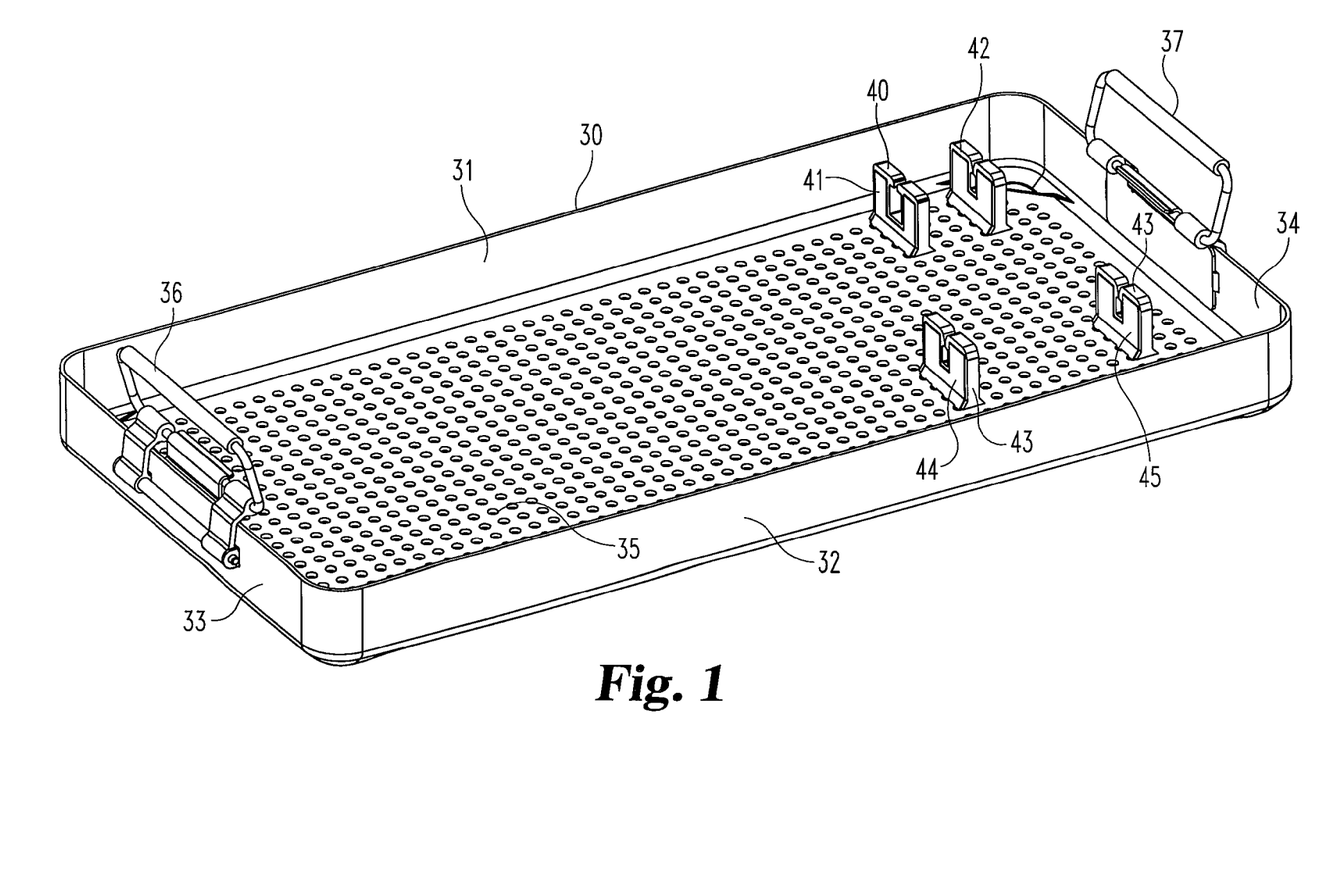
FIG. 1 is a perspective view of a sterilization container having the brackets or holders for securing medical items within the container.

Referring now more particularly to FIG. 1, there is shown the preferred embodiment of a sterilization container 30 for holding medical items therein by a plurality of brackets. A lid (not shown) is removably mounted to the container prior to insertion of the container into the sterilization process.

Container 30 has a pair of side walls 31 and 32 joined to a pair of end walls 33 and 34 all, in turn, joined to a perforated floor 35. Such a container is disclosed in our issued U.S. Pat. Nos. 7,341,148 and 7,717,264 which are herewith incorporated by reference in their entirety. The container is used for the organization, protection, sterilization, storage and delivery of surgical instruments, implants and related devices. The optional perforated cover disclosed in our incorporated patents is removably secured thereto by a pair of handle assemblies 36 and 37.

In our U.S. Pat. No. 7,717,264, we have disclosed an extruded flexible wall mounted to a pair of brackets, in turn, mounted to the base for partitioning the compartment formed by the container for holding medical instruments and/or implants. The pair of brackets extend immediately adjacent and in contact with the outwardly extending bottom portion of the extruded flexible wall. Each bracket has inwardly turned feet that may be extended through holes in the floor of the container and then adjacent and against the bottom surface of the container thereby securing the flexible wall to the container floor.

Disclosed herein is a composite holder including a flexible wall secured on either side by upwardly extending rigid walls with fasteners extending through the rigid walls into the top portion of the flexible wall. Each wall has outwardly turned feet. The result is a sturdy holder that is held together at its top end by the fasteners extending through the brackets and flexible wall and on the bottom end by the outwardly turned feet.

Two pairs of brackets incorporating our new features are shown in FIG. 1. The first pair 40 of brackets consist of two holders 41 and 42 removably mounted to the perforated floor 35 and a second pair of holders 43 consisting of holders 44 and 45 also removably mounted to the perforated floor. It is to be understood that many more holders may be mounted to the perforated floor depending upon the actual requirements and the number of surgical instruments and/or implants to be held within the container. Holders 41 and 42 are aligned forming pair 40 whereas holders 44 and 45 are aligned forming pair 43.

Figure 2:
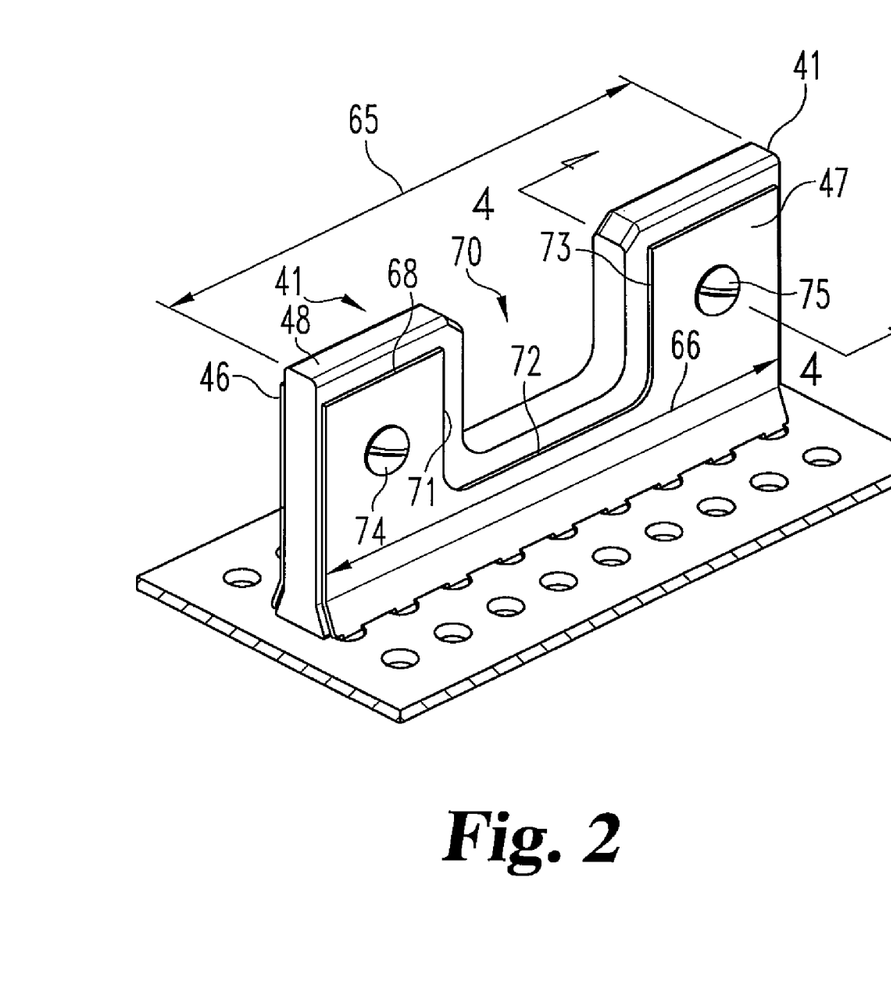
FIG. 2 is an enlarged perspective view of one of the brackets mounted to the floor of the container of FIG. 1.
Figure 3:
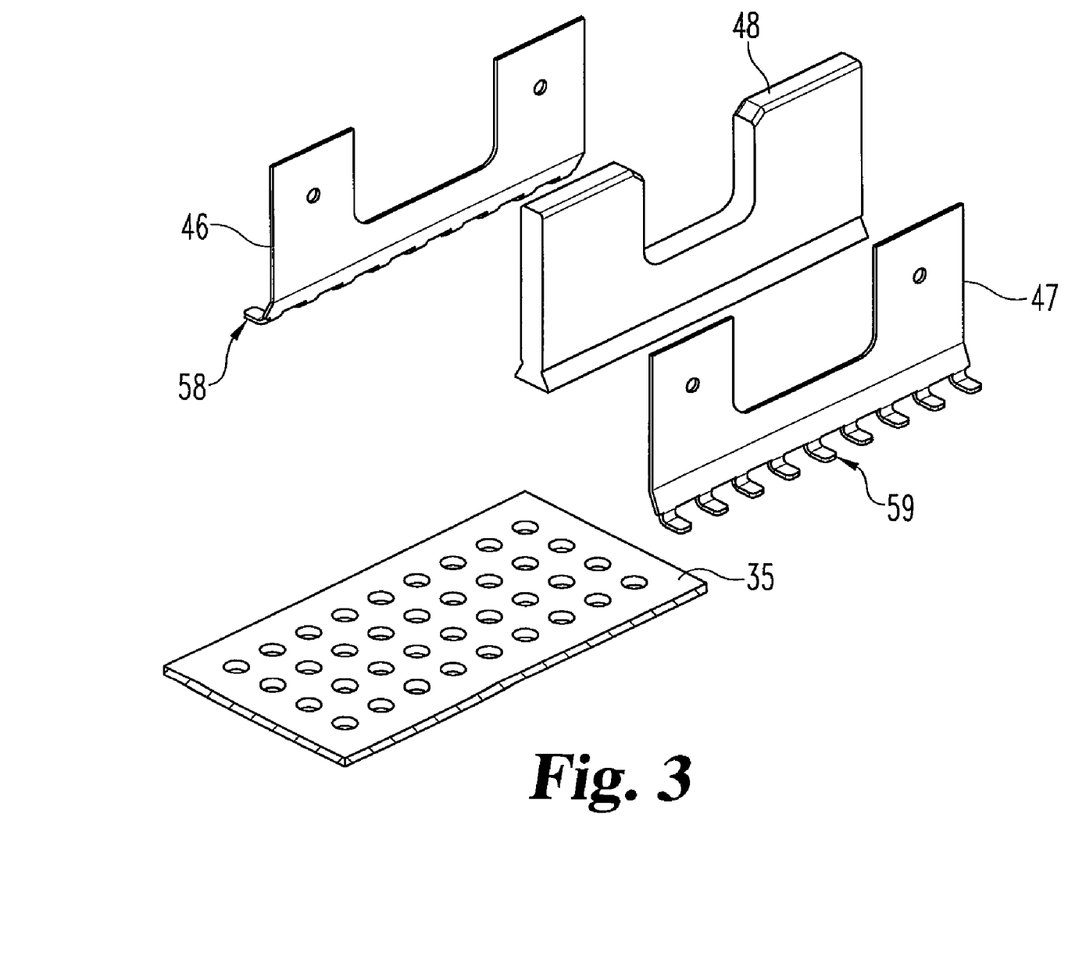
FIG. 3 is the same view as FIG. 2 only is an exploded view.
Figure 4:
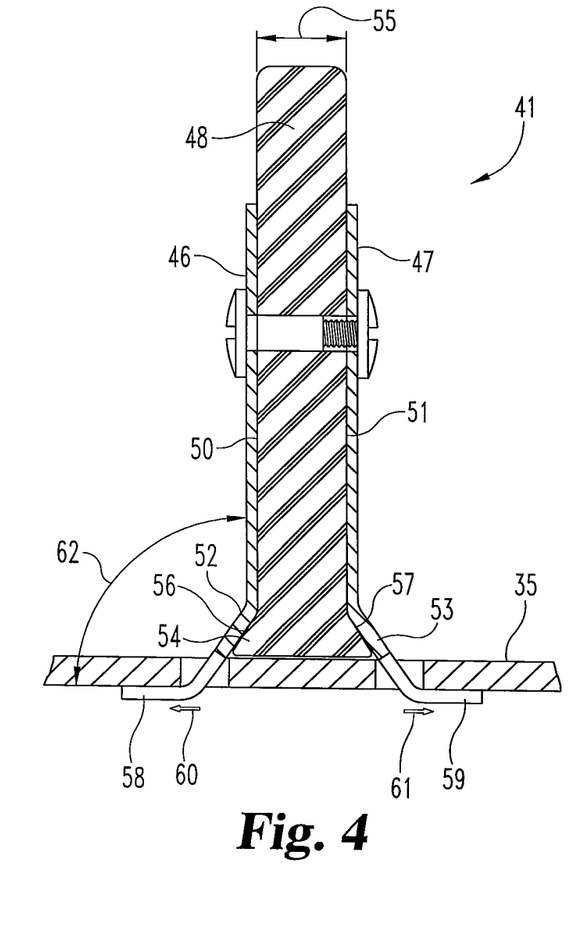
FIG. 4 is a cross-sectional view taken along the line 4-4 of FIG. 2 and viewed in the direction of the arrows.
Figure 5:
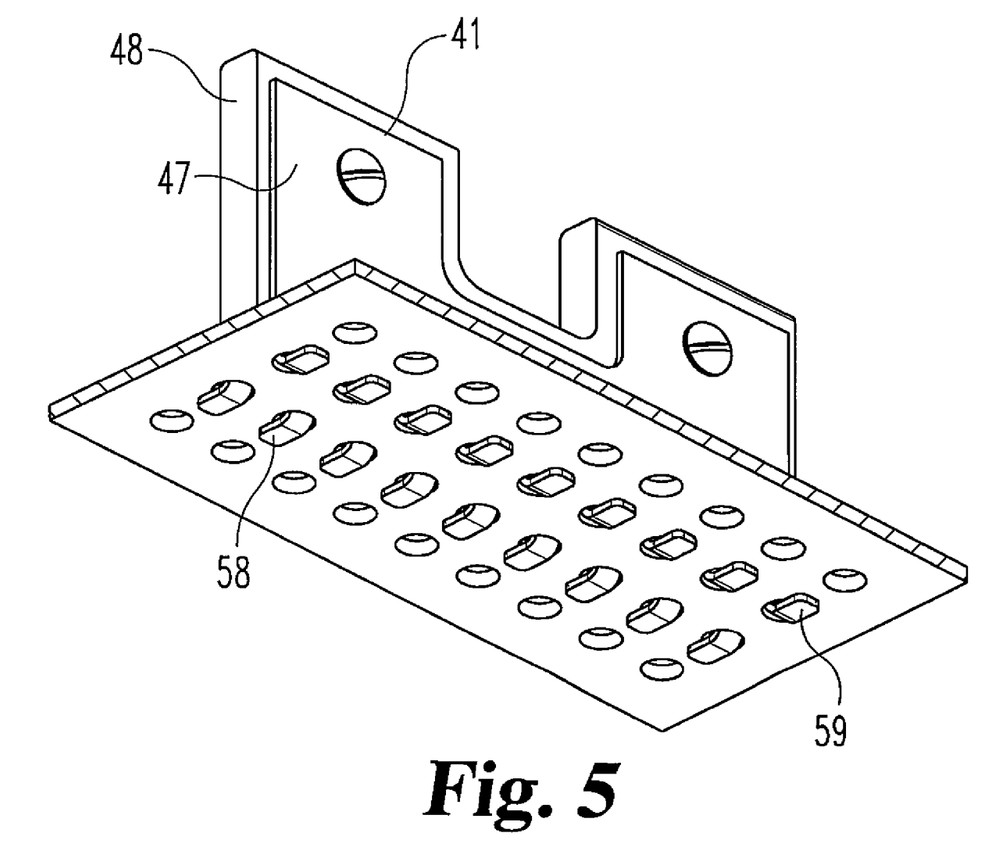
FIG. 5 is a bottom perspective view showing the bracket feet secured to the container floor.

Holder 41 (FIG. 2) will now be described it being understood that an identical description applies to the remaining holders. The composite bracket arrangement or holder 41 has identical brackets 46 and 47 between which is located an elongated bar or wall 48 of flexible material. Brackets 46 and 47 have rigid main bodies with a plurality of feet integrally attached thereto and extending beneath each bracket main body in an outward direction. Referring to FIG. 4, brackets 46 and 47 have vertically extending main bodies 50 and 51 that have intermediate wall portions 52 and 53 with each diverging outward to conform to the dove tail outwardly extending bottom end portion 54 of the elongated bar 48. The width 55 of bar 48 is constant except when the width increases at the bottom end portion 54 forming two outwardly facing surfaces 56 and 57. A plurality of feet 58 and 59 are respectively integrally joined by intermediate wall portions 52 and 53 with the main bodies 50 and 51 of the two brackets. While the main bracket bodies 50 and 51 are parallel, feet 58 extend in the direction of arrow 60 whereas feet 59 extend in an outward opposite direction as shown by arrow 61. Feet 58 are arranged at an included angle 62 of approximately 90 degrees relative to main bracket body 50 so that when first intermediate connecting portion 52 is extended through the base wall or floor 35, feet 58 position main body 50 above floor 35 and arranged perpendicularly with respect to the floor. Likewise, feet 59 are arranged relative to the bracket main body 51 at an included angle of approximately 90 degrees so that when the second intermediate connecting portion 53 is extended through floor 35, position bracket main body 51 above the floor and arranged perpendicularly thereto. Brackets 46 and 47 have an equal thickness with the main bodies 50 and 51 intermediate connecting portions 52 and 53 and feet 58 and 59 having the same thickness. Since the included angle 62 between feet 58 and bracket main body 50 is the same as the included angle between feet 59 and bracket main body 51, they automatically position main bodies 50 and 51 in parallel relationship. Intermediate portions 52 and 53 extend angularly through the holes in floor 35 and bind against the hole edges of floor 35 forcing the connecting portions 52 and 53 to squeeze the flexible wall 48.

Flexible wall 48 has a length 65 (FIG. 2) that extends along and beyond the length 66 of brackets 46 and 47. The wall may be produced from a flexible material, such as silicone rubber whereas brackets 46 and 47 may be produced from a rigid material such as metal or hardened plastic. The height of wall 48 extends above the top edge 68 of brackets 46 and 47 and also extends beyond the length of brackets 46 and 47. Thus, wall 48 provides a cushioned wall that extends beyond the periphery of brackets 46 and 47 thereby limiting any damage to the surgical instruments or implants that contact the composite bracket. Both wall 48 and the main bodies of brackets 46 and 47 are provided with an aligned recess 70 to removably receive the surgical instrument or implant. Recess 70 has a general cylindrical bottom portion joined to a pair of upstanding vertical portions forming an upwardly opening recess. Wall 48 extends inwardly of edges 71, 72 and 73 of brackets 46 and 47 thereby also providing a cushioned wall extending into the recess beyond the edge of the brackets again limiting damage to the surgical instrument or implant as it is inserted into the recess.

A plurality of fasteners extend through bracket 46, wall 48 and bracket 47 securely holding the wall between the main body of brackets 46 and 47. In the embodiment shown in FIG. 2, two such conventional fastening devices 74 and 75 are shown it being understood that a greater or less number of fasteners may be utilized. The fasteners are located in the upper portion of the composite bracket thereby holding the top portions of the main bodies securely to the top portion of wall 48. A variety of commercial fasteners may be utilized. For example, excellent results have been achieved by using a fastener with a head positioned on the outwardly facing side of bracket 47 having an externally threaded stem that extends through wall 48 and into an internally threaded stem having a head positioned on the outwardly facing surface of bracket 46.

Figure 6:
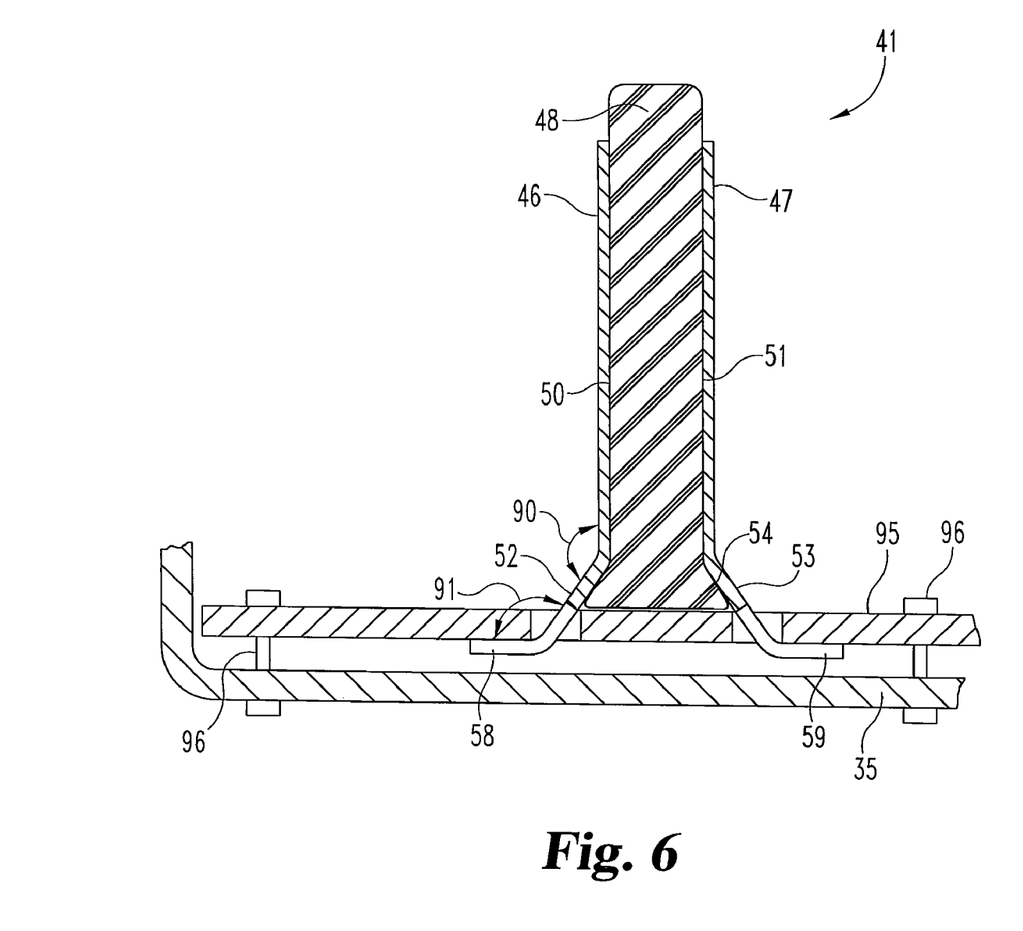
FIG. 6 is the same view as FIG. 4 only showing the bracket mounted to a sub-floor, in turn, mounted to the floor of the container of FIG. 1 with the cross section being taken at a location other than where the fasteners 74 and 75 are located.

When assembling the brackets 46 and 47 to wall 48, it is important that the holes in brackets 46 and 47 and wall 48 receiving fasteners 74 and 75 be aligned so that the flexible wall extends beyond the main bodies of walls 46 and 47 for forming a flexible contact edge for medical items to be held by the bracket arrangement. Thus, the main bodies 50 and 51 (FIG. 4) have horizontally top edges and vertically extending side edges extending downwardly from the horizontal extending top edges with both the horizontal extending edges and the vertically extending edges located inwardly from the flexible contact edge of the elongated wall. The interconnecting portions 52 and 53 integrally joining the main bodies 50 and 51 (FIG. 6) of brackets 46 and 47 are each arranged at an obtuse angle 90 (FIG. 6) relative to the bracket main bodies. Likewise, interconnecting portions 52 and 53 are arranged respectively to feet 58 and 59 at an obtuse angle 91.

The holes in the perforated walls are arranged so that when interconnecting portions 52 and 53 are extended there through, the feet contact the bottom surface of the base resulting in the interconnecting portions 52 and 53 tightly squeezing the enlarged bottom portion 54 of flexible wall 48 thereby cooperating with fasteners 74 and 75 to tightly grip the flexible wall 48 between brackets 46 and 47.

While the preferred embodiment has been shown in FIGS. 1-5, the present invention also includes providing a sub-wall 95 spaced apart from the container floor 35 but being held thereto by plurality of standard fastening devices 96. In such a case, brackets 46 and 47 are installed on the sub-wall 95 by extending the interconnecting portions of each bracket through wall 95 with the feet then being spaced apart from the container floor 35.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A bracket arrangement to hold medical items on a base wall for sterilization thereof comprising:
    a first bracket having a rigid first main body with a plurality of first feet integrally attached thereto and extending there beneath in a first outward direction from said first main body at an approximate first included angle of ninety degrees so that when said first bracket is extended through said base wall and arranged therewith, said first main body is above said base wall and arranged perpendicular to said base wall;
    a second bracket having a rigid second main body spaced apart from said first main body and having a plurality of second feet integrally attached thereto and extending there beneath in a second outward direction opposite to said first direction and away from said first plurality of feet at an approximate second included angle relative to said second main body of ninety degrees so that when said second bracket is extended through said base wall and arranged therewith, said second main body is above said base wall and arranged perpendicular to said base wall;
    an elongated bar of flexible material extendable along a length of said first bracket and said second bracket and positioned there between; and,
    a plurality of fasteners extending through said first bracket, said elongated bar and said second bracket, thereby securing the first bracket, the elongated bar and the second bracket together; and wherein:
    said first main body, said second main body, said plurality of first feet and said plurality of second feet are of equal thickness with said first feet and said second feet extendable through said base wall for securing the bracket arrangement thereto;
    said first included angle and said second included angle are equal, and position said first main body and said second main body in a parallel relationship;
    said elongated bar extends outwardly beyond said rigid first main body and said rigid second main body, thereby providing a flexible contact edge for medical items to be held by the bracket arrangement.

2. The bracket arrangement of claim 1 wherein:
    said rigid first main body and said rigid second main body include horizontally extending edges and vertically extending edges extending downward from said horizontally extending edges with said horizontally extending edges and said vertically extending edges located inwardly of said flexible contact edge of said elongated bar.

3. The bracket arrangement of claim 2 wherein:
    said elongated bar has a upwardly opening recess extending below said horizontally extending edges with said flexible contact edge extending outwardly of said first main body and said second main body in said recess for limiting contact between said first bracket and said second bracket when a medical item is positioned in said recess.

4. The bracket arrangement of claim 1 wherein:
    said first bracket has a first connecting portion integrally connecting and positioned between said first main body and said plurality of first feet, said first connecting portion arranged at a first obtuse angle relative to said first main body and a second obtuse angle relative to said plurality of first feet; and,
    said second bracket has a second connecting portion integrally connecting and positioned between said second main body and said plurality of second feet, said second connecting portion arranged at a second obtuse angle relative to said second main body and a fourth obtuse angle relative to said second feet; and, said elongated bar has an enlarged lower portion located between and releasably held by said first connecting portion and said second connecting portion.

5. The bracket arrangement of claim 4 wherein:

said elongated bar has an enlarged bottom portion with said first connecting portion and said second connecting portion extending angularly through holes in said base wall and binding against said base wall and tightly squeezing said enlarged lower portion of said bar with said first feet and said second feet positioned adjacent said base wall; and, said first main body and said second main body include top portions through which said fasteners extend, thereby tightly squeezing said top portions to said elongated bar.

6. The bracket arrangement of claim 5 wherein:

said bar is silicone rubber and said first bracket and said second bracket are metal or plastic.

7. A sterilization container for holding medical items therein comprising:

a five sided tray having a base with holes extending through said base, said tray further having upwardly extending side walls for placing medical items therein for sterilization; and, a plurality of bracket combinations removably mounted to said base for releasably holding said medical items within said tray, each bracket combination including a pair of brackets separated from each other with mutually opposed and spaced apart vertically extending walls each with outwardly turned feet and with said brackets extending through said holes of said base, thereby holding said vertically extending walls perpendicular relative to said base with said feet integrally attached to said vertically extending walls and positioned adjacent said base, an elongated silicone bar located between said vertically extending walls, and a plurality of fasteners extending through said bar and said vertically extending walls and tightly securing said vertically extending walls to said bar, wherein each said vertically extending wall has a length and a height with said bar extending along and beyond said length and along and beyond said height, thereby providing a cushion edge portion outwardly said extending beyond vertically extending walls.

8. The sterilization container of claim 7 wherein:

said vertically extending walls and said bar have a recess into which a medical item may be held with said cushion edge portion extending outwardly of said vertically extending walls within said recess.

9. The sterilization container of claim 8 wherein:

said brackets have connecting portions with end portions integrally connected to said vertically extending walls and opposite end portions integrally connected to said feet, said connecting portions arranged at first obtuse angles relative to said vertically extending walls and second obtuse angles relative to said feet to position the feet relative to said vertically extending walls at an included angle to maintain perpendicularity of said vertically extending walls relative to said base while squeezing said bar.

10. The sterilization container of claim 9 wherein:

said bar is flexible and has an enlarged bottom end portion terminating at a bottom end with opposite and outwardly facing side surfaces that diverge in a direction toward said bottom end, said side surfaces arranged at obtuse angles which are the same as said first obtuse angles.

11. The sterilization container of claim 10 wherein:

said brackets extend angularly through said holes and bind against said base forcing said connecting portions to squeeze said bar with said feet outwardly extending relative to said brackets.

* * * * *